United States Patent [19]

Axén et al.

[11] Patent Number: 4,535,010

[45] Date of Patent: Aug. 13, 1985

[54] METHOD OF FORMING POLYMERIC LAYERS

[75] Inventors: Rolf E. Axén, Bälinge; Göran L. Kaj; Bror S. Rigner, both of Uppsala, all of Sweden

[73] Assignee: Pharmacia AB, Uppsala, Sweden

[21] Appl. No.: 542,507

[22] Filed: Oct. 17, 1983

[30] Foreign Application Priority Data

Oct. 18, 1982 [SE] Sweden ................. 8205908

[51] Int. Cl.³ .............................. B05D 5/00
[52] U.S. Cl. .................................. 427/246; 427/245; 210/490; 210/500.2
[58] Field of Search ............... 427/246, 245; 210/490, 210/500.2

[56] References Cited

U.S. PATENT DOCUMENTS 4,207,128  6/1980  Träubel et al. ............... 427/246 X
4,387,024  6/1983  Kurihara et al. ............. 427/245 X
4,388,189  6/1983  Kawaguchi et al. .......... 427/245 X

FOREIGN PATENT DOCUMENTS 50-25892  3/1975  Japan ................. 427/245
57-91706  6/1982  Japan ................. 427/245
57-91707  6/1982  Japan ................. 427/245

Primary Examiner—Thurman K. Page
Attorney, Agent, or Firm—Fred Philpitt

[57] ABSTRACT

In the formation of polymeric layers, especially anisotropic polymeric layers, on a solid substrate on which the layer is formed by cross-linking of an organic substance which can be cross-linked, the cross-linking is performed in a manner such that a concentration gradient of at least one of the components controlling the cross-linking reaction is formed in the boundary layer between the substrate to be coated and the surrounding solution, which concentration gradient is adjusted so that cross-linking can take place in the boundary layer but not in the surrounding solution. The concentration gradient is preferably achieved by impregnating the substrate with at least one of the components which control the cross-linking reaction and which tends to diffuse into the solution on contact therewith.

12 Claims, No Drawings

METHOD OF FORMING POLYMERIC LAYERS

The present invention relates to a method of coating a solid body or substrate with polymeric layers which are formed by cross-linking an organic substance which can be cross-linked.

It is desirable in a great number of biomedical and biotechnological fields to be able to change the surface properties of a solid body or substrate, so that the body/substrate becomes more suitable for the intended application and/or can be used for other purposes than is possible with the surface properties of the untreated substrate. A few examples of fields of technology in which a change of the surface properties can be desirable are in connection with solid substrates intended for various types of chromatography, determination methods comprising biospecific affinity reactions between a receptor and a ligand (e.g. between an antibody and an antigen or a hapten), enzymatic assaying methods (for enzymes, co-enzymes, co-factors, etc.), support phases for electrophoresis, in general for forming biocompatible surfaces, for "biochemical engineering", and so on.

Bodies or substrates for use in these fields have previously been provided with a surface coating i.a. by first adsorbing a compound containing hydroxyl or amine groups (e.g. a polysaccharide or a protein) on the solid substrate, and then cross-linking the adsorbed compound. An alternative known method is to covalently bind reactive structures to the surface of a solid substrate, whereafter the reactive structures are used for binding polymeric compounds to the surface.

A short summary of the state of the art for surface modification in other fields of technology can be found in Tatzuke S et al, Makromol Chem. 179 (1978), p. 2603-04.

Surface coating thus means that new properties are provided on the surface of a solid substrate. Many times one only wants to emphasize the properties of the applied surface layer and at the same time conceal any effect of the original surface properties of the substrate or body. In i.a. the above indicated fields of application one also often wants to make use of properties which are present within the applied layer. By forming an applied layer, which is porous and hydrophilic and can be swelled to gel form, different macromolecular biomolecules can easily penetrate the layer without their biological activity being destroyed. The porosity also makes the effective area considerably larger than the surface area of the uncoated body or of a body provided only with a mono-molecular layer. The penetration capability is, of course, dependent on the degree of cross-linking.

The present invention relates to a novel and improved method of preparing such surfaces, which method makes it possible to control the degree of cross-linking of the applied surface layer, whereby the properties of the underlying substrate surface can be "concealed" and the properties of the surface layer be varied as desired. By means of the novel method of application the surface layers can be formed in a very reproducible and controllable manner. The method in particular makes it possible to form antisotropic layers, i.e. layers whose degree of cross-linking—and consequently physical/chemical properties etc.—varies from one side of the layer to the other side thereof, e.g. with a decreasing degree of cross-linking from the substrate outwards.

The novel method according to the invention has the characterizing features which are indicated in the subsequent claims and which are explained further below.

In the method according to the invention one thus forms a polymeric surface layer on a solid substrate, which is to be modified on the surface, by cross-linking of an organic substance capable of being cross-linked. According to the invention the cross-linking is carried out in a manner such that there is created a concentration gradient of at least one of the components, which control the cross-linking reaction, in the boundary layer between the substrate to be coated and the surrounding solution, the concentration gradient being so adjusted that cross-linking can take place in said boundary layer but not in the surrounding solution. The layer is thus always formed by cross-linking close to the surface of the substrate. A newly fomed layer can in turn be regarded as a substrate which can be coated in accordance with the invention.

By expressions such as "components controlling the cross-linking reaction", "the components necessary for the cross-linking reaction" and the like is herein meant not only the organic substance or substances to be cross-linked and the cross-linking agent, but also other factors necessary for making it possible for the cross-linking reaction to take place in the indicated manner. Such factors will be discussed further below under the term "modulator".

According to a preferred embodiment of the method said concentration gradient in the boundary layer between the substrate and the surrounding solution is provided by pre-impregnating the substrate with at least one component which is necessary for the cross-linking reaction and which, on contact with said solution, tends to diffuse into the same. For example, the substrate can be impregnated with the cross-linking agent, which on contact with said solution diffuses into the same, where the conditions are such that cross-linking cannot take place, e.g. because the cross-linking agent is inactivated in the solution or the cross-linking reaction is otherwise prevented. The cross-linking therefore only takes place in the boundary layer, and then usually with a stronger cross-linking closest to the substrate and with reduced cross-linking towards the surrounding solution. Another example is to impregnate the substrate with a modulator substance, e.g. hydroxyl ions, which diffuses into the solution and in the boundary layer contacts the other cross-linking components which all together determine the cross-linking conditions at that very place, whereas the conditions in the very solution (which in this case usually contains the cross-linking agent) are not changed and therefore do not permit cross-linking. Also e.g. the organic substance which can be cross-linked can be impregnated in the substrate, in particular when it is low molecular such as sugar alcohol.

By "is impregnated in the substrate" is herein meant that the impregnated cross-linking component or components can be taken up by the substrate and then be released in the indicated manner when the impregnated substrate is brought into contact with said solution. The substrate is usually a solid solvent, preferably organic, for the components to be impregnated, but the invention also comprises impregnation in a different manner, e.g. uptake in the pores of a porous substrate. The substrate can also be pre-impregnated with a solvent which affects the uptake and release of the impregnated component. Such a solvent can during the coating procedure be transported into the surrounding solution and affect th cross-linking in the boundary layer.

The above mentioned "surrounding solution" is preferably aqueous, and the expression is intended to cover also e.g. colloidal solutions and the like which form a substantially homogenous reaction medium.

The theoretical explanation of the properties of the layers has not yet been made clear, but it probably depends on the fact that the layers have a cross-linking gradient. One explanation of the creation of such a gradient is that the rate of cross-linking is a function of local concentrations close to the surface of the body of at least one of the components which affect the cross-linking reaction and thus gives rise to a cross-linking gradient.

The different components cross-linking agent, modulator, substrate, organic substance which can be cross-linked (reactant) and solvent will now be discussed further.

Cross-linking agent (T)

The cross-linking agent can be a compound having at least two electrophilic groups which react irreversibly with hydroxyl and/or amino groups of the reactant (R). By "irreversibly react" is herein meant that the directly formed product of the reaction between an electrophilic group and an amino or hydroxyl group is stable, but also the forming of unstable products, which are stabilized, is comprised by this term. Of the amino groups primary, secondary or tertiary ones are preferred. The cross-linking agent preferably contains two hard electrophilic groups which directly give a stable product in their reactions with two hydroxyl or two amino groups or two different such groups. The cross-linking agent is thus preferably bifunctional. The functional groups of the cross-linking agent are in this case chosen such that the molecules of the reactant mainly are bonded together via amide, amine and/or ether bonds in the formed layer, but also ester bonds of the same hydrolytic stability can be accepted. Imidocarbonate structures can be mentioned as examples of the latter. Also the corresponding thio congeners can be used.

Bifunctional cross-linking agents which can be used according to the invention can be divided into two groups;

a. Those which structurally contain only one functional group but react as if they contained two. In this case there is formed a reactive structure in the reaction between the cross-linking agent and an amino or a hydroxyl group, which reactive structure reacts further with a further amino or hydroxyl group. Examples of cross-linking agents of this types are cyanhalides, preferably cyan bromide, lower alkyl or aryl sulphonyl chloride as well as the carbonic acid derivatives phosgene and N,N'-diimidazolcarbonyl.

b. Those which structurally contain two functional groups which can react with hydroxyl and/or amino groups. In general this type can be written as

X—A—Z wherein A can be a lower alkyl or aryl chain having less than ten carbon atoms, preferably less than seven carbon atoms. A is always a hydrocarbon chain which is not destroyed under the conditions of the cross-linking. The hydrocarbon chain is in many common bifunctional cross-linking agents possibly substituted with preferably 1-3 hydroxyl groups and is possibly interrupted by 1-3 ether or ester bonds.

X and Z are usually the same, but they can in certain instances be different. Examples of X and Z are; —N=C=S, —COY (wherein Y can be halogen, S-2-thiopyridyl or nitro or carboxyl substituted such pyridyl group), —CNHOR' or corresponding acid addition salts (wherein R' is a lower alkyl or aryl group preferably having less than three carbon atoms),

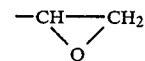

or a corresponding halogen hydrin. In those cases when X is oxiran or halogen hydrin and A is methylene, Z can advantageously be chosen as halogen, preferably chlorine.

Many of the above mentioned cross-linking agents interconnect hydroxyl and/or amino group-containing reactants (R) with each other via hydrocarbon bridges in the formed surface layer. In the examples below there is indicated if a bridge has been formed and the relevant bond structure.

| Cross-linking agent or functional group | Bond structure | Bridge |
|---|---|---|
| Cross-linking agent | | |
| Cyan halide | amide or ester | imidocarbonyl |
| N,N'—dimidazol-carbonyl | amide or ester | carbonyl |
| phosgene | amide or ester | carbonyl |
| Functional group | | |
| —N=C=S | thio carbamate or thio amide | hydrocarbon residue |
| —COY | ester or amide | hydrocarbon residue |
| —CHCH₂ \O/ | ether, amine | hydroxyalkylene |
| Halogenhydrin | ether, amine | hydroxyalkylene |
| Halogen | ether, amine | hydrocarbon residue hydroxyalkylene when A=CH₂ and the cross-linking agent also has oxiran or halohydrin |

The formed bond structure is, of course, dependent on if a hydroxyl or an amino group has reacted with the cross-linking agent. Amino groups give amide or amine structures, and hydroxyl groups give ester or ether structures. It also appears from the table that certain cross-linking agents introduce hydrophilic hydroxy alkylene groups, which is a great advantage. Hydrocarbon groups otherwise reduce the hydrophility of the polymeric layer which is formed.

An essential property of the cross-linking agents to be used according to the invention is that they are soluble in the aqueous solvent used. Furthermore, the cross-linking agent should, in its most preferred embodiment, be soluble in the substrate.

In the embodiment in which the substrate is a porous body, the pores are filled with an aqueous solution of the cross-linking agent. The body is then immersed into an aqueous solution of a suitable pH containing the reactant (R) to be cross-linked and the modulator (M). The diffusing cross-linking agent is destroyed in this aqueous solution, but closest to the surface of the body the cross-linking agent will be able to react the reactant (R) so that the surface of the body is coated.

A very advantageous embodiment is to dissolve so much of the cross-linking agent in the body that the concentration gradient remains substantially constant during the surface coating process. Such a procedure provides a very safe way of controlling the reaction. A person skilled in the art can very easily check which combinations of substrate (material, shape, and so on) and cross-linking agent are suitable, by determining the solubility or impregnation capability of the cross-linking agent in the body and the ability of the cross-linking agent to distribute between the body and the aqueous solution in which the surface coating is performed. See the discussion under the description of the substrate (S) below.

A further property of the cross-linking agent is that it should be possible to affect its reaction velocity with the reactant (R). This can be done by, for example, adding to the aqueous solution mono-functional nucleophilic reagents such as hydroxide or thiosulphate ions or low molecular primary, secondary or tertiary amines. The mono-functionality makes them uncapable of being built-in as bridges in the polymeric layer. In all of these cases there is often a matter of irreversibly destroying the cross-linking agent. The above described lower molecular nucleophilic reagents will in the following be called modulators.

The solvent (L)

This is aqueous having a buffer dissolved therein which can affect the modulator. The pH of the solution can be varied on the one hand with regard to the cross-linking agent used, and on the other hand with regard to the hydroxyl or amino group-containing compound to be cross-linked. In an advantageous embodiment a buffer having a high buffer capacity is used, so that no pH gradient can be occur closest to the substrate (S). A high buffer capacity renders the creation of local pH variations more difficult. One can thus more easily control the reaction by using a high buffer capacity.

The modulator (M)

The modulator affects the reaction velocity between the reactant (R) and the cross-linking agent (T) in mainly two different ways:

a. by affecting the reactivity of the nucleophilic groups, preferably the reactivity of hydroxyl and/or amino groups. A lowering of the pH can convert e.g. an amino group to an ammonium group, which in turn has great difficulties in reacting with the electrophilic cross-linking reagent. This type of change of the reactivity is reversible, but also irreversible changes can be contemplated.

b. by affecting the reactivity of the cross-linking agent. This is preferably done in an irreversible way by reacting the cross-linking agent with strong nucleophils which preferably are mono-functional, e.g. hydroxide ions, thiosulphate ions, ammonia or low molecular primary, secondary or tertiary amines.

The concentration of hydroxide ion, ammonia and amine are all pH dependent. This means that the cross-linking velocity can be controlled by means of the pH, which in turn can be controlled by means of various buffers. By modulators is herein meant such entities as directly affect the reactivity of the cross-linking agent (T) or of the reactant (R). Preferred modulators are protons ($H^+$, $H_3O^+$), hydroxide ions ($OH^-$), primary, secondary and tertiary amines. The reactivity can be affected by e.g. protonisation or deprotonisation of an amine and of ammonium groups respectively. In a preferred embodiment the cross-linking agent is destroyed irreversibly, preferably by hydrolysis. Thiosulphate can be used primarily for destroying cross-linking agents having epoxide or halogenhydrine groups.

In one embodiment the modulator (M) and the reactant (R) are dissolved in the solvent. The modulator concentration and pH is adjusted such that cross-linking does not occur in the solution, but only close to the surface of the body, where the concentration of the cross-linking agent is sufficiently high because of diffusion from the substrate.

In a preferred embodiment the modulator concentration is so high that it does not diminish because of the reaction between the cross-linking agent and the modulator. In this embodiment the cross-linking velocity will only be dependent on the diffusion of the cross-linking agent from the substrate. The surface coating can in this case be performed in a very reproducible and controllable manner.

In one embodiment the modulator is dissolved in the substrate (S). This can be done e.g. by swelling a porous, cross-linked dextran particle in sodium hydroxide solution. The reactant (R) and the cross-linking agent (T) are dissolved in the solvent (L) at such pH that they do not react with each other. When the substrate (S) is immersed in the solvent the modulator diffuses out starting the cross-linking reaction while at the same time a competing reaction between the modulator and the cross-linking agent inactivates the latter. In the case with the above mentioned dextran particle the pH of the solvent (L) is chosen so low that cross-linking cannot occur in the solution. When hydroxide ions migrate from the particle the pH of the solution is increased so that the cross-linking starts. At the same time the competing destruction of the cross-linking agent (T) starts.

A very suitable modulator is the above mentioned hydroxide ion, but in certain cases the other of the mentioned modulators (or analogous modulators) can be suitable. In aqueous solutions both ammonia and hydroxide ions can coexist, i.e. several modulators can be present at the same time in the solution. This, of course, also applies to $H_3O^+$ and $OH^-$, the concentrations of which are determined by the pH of the surrounding solution. It is not necessary to add the modulator substances as such, but they can be formed by the addition of other compounds. For example, the concentration of $OH^-$ and $H_3O^+$ can be changed by the addition of acids or bases.

The reactant (R)

The reactant (R) preferably has at least three amino and/or hydroxyl groups. Examples of useful compounds are primarily various water soluble or water suspendible polysaccharides and soluble derivatives of insoluble polysaccharides. As examples of polysaccharides can be mentioned dextran, cellulose, starch, agarose, amylose, and so on. The polysaccharides may be substituted with hydroxyalkyl or ion exchange groups such as primary, secondary, tertiary or quaternary amine groups. Other examples of ion exchange groups are those containing a sulphonic acid or carboxylic acid structure. In such a case the substitution must not have destroyed the ability of the reactant to react with the cross-linking agent. Of low molecular compounds which can be used according to the invention can be mentioned various sugar alcohols such as sorbitol, mannitol, xannitol and glycerol, as well as mono, di and oligo saccharides. Also e.g. proteins can be used as a reactant in the invention. Additional examples are heparin or hyaluronic acid.

The substrate (S)

The substrate (S) may in principle have any form and it may furthermore be porous. It can be coated on all sides or parts thereof, only on one side, etc. Hollow bodies can e.g. be coated only on the inside, only on the outside or both. The same applies to porous bodies. The form of the substrate will be discussed further under the various fields of application.

The choice of material for the substrate is of great importance for a successful surface coating. Thus at least one of the components, preferably the cross-linking agent (T) or the modulator (M), ought to be soluble—or capable of being impregnated—in the substrate and be distributed from the same and/or from its pores out into the solvent when performing the coating. Usually, some kind of plastics such as Plexiglass ® (polymethylmethacrylate), polystyrene, polyvinylalcohol, polyvinylchloride, polyethylene or the like is chosen. For certain fields of application it can be suitable to use porous substrates, whose uptake of cross-linking agent or modulator is increased in that solutions of the latter can be absorbed in the pores of the porous substrate (during the coating process the cross-linking agent/modulator then diffuses out from the pores). Examples of porous substrates are the very well known gel chromatographic mediums Sephadex ®, which consists of cross-linked dextran, and Spheron ®, which consists of cross-linked poly(hydroxyalkyl methacrylate).

Certain of the above mentioned substrates are built up from compounds containing nucleophilic groups, e.g. hydroxyl groups. Layers formed on such substrates can be covalently bonded to the substrate by means of the electrophilic cross-linking agent. The surface of the substrate can be etched by means of e.g. acid or alkali in order to increase the adhesive ability of the layer.

By adsorption and distribution tests it can easily be determined if a certain substrate is suitable with regard to the solubility of the cross-linking agent or the modulator. The test method used for measuring the capability of taking up the cross-linking agent in the substrate is, of course, dependent on the type of cross-linking agent. E.g. an epihalohydrin can be soaked from the substrate by means of sodium hydroxide solution, followed by an argentometric titration. This can also be done with e.g. cyanbromide. If the substrate is transparent the measurement can be performed spectrophotometrically.

A few different fields of application for the surface coated products according to the invention will now be discussed.

In chromatography the products according to the invention can be used as support phases in different types of liquid chromatography such as ion-exchange, affinity and gel chromatography. The chromatography can be carried out both at high and normal pressures. In chromatographic applications the coated substrates most often have the form of particles, preferably monodisperse spheric particles, but also the inside of chromatographic columns can be treated according to the invention. Porous particles can be surface coated both on the inside and the outside. Different ion-exchange groups and ligands for affinity chromatography can be coupled to the layers in usual manner. Plates can also be coated for being used in thin layer chromatography.

In determination methods involving biospecific affinity reactions between a ligand and a receptor, one of these reactants is often bonded to the applied surface layer. In these methods there is often included a reactant which is labelled with an analytically indicatable group or atom. Examples of such assaying methods between a ligand and a receptor are various agglutinations, enzyme immunological and radio immunological tests. The form of the coated substrate can in this field of application be particulate or disc-shaped, but also the walls of the reaction vessels can be coated.

In enzymatic determination methods the three dimensional network, which has been prepared according to the invention, can form a substrate for an enzyme, soluble fragments being released by the effect of the enzyme. If the layer is provided with analytically indicatable groups, these soluble fragments can then be detected when the substrate is separated from the solution. Enzyme substrates for hydrolytic enzymes can advantageously be prepared. By cross-linking a polysaccharide e.g. enzyme substrates for endoglycosidases can be prepared, which degrade the cross-linked polysaccharide. What has been said above about the form of the coated substrate is applicable also here.

Biocompatible surfaces can be prepared by using suitable hydroxyl-and/or amino group-containing compounds and cross-linking reagents. Examples of such surfaces are heparin-coated tubes and hoses for preventing blood coagulation. Other examples are treatment of vessels, tubes and particles to be used in the above mentioned determination methods. In these latter cases the non-specific adsorption can be reduced.

Substrates which have been coated in accordance with the invention can also be used in so-called biochemical engineering. In these cases, for example a component in an enzymatic system can be made insoluble to a substrate surface coated in accordance with the invention. The particles can then be placed in a so-called enzyme reactor, and the end product of the enzymatic reaction can be recovered. Of course, the walls of the reactor can also be coated according to the invention. Also micro-carriers for cell cultivation can be prepared in accordance with the invention.

The following concrete examples illustrate how the invention can be carried out in practice, but it should be underlined that the invention is not intended to be limited to these embodiments.

EXAMPLE 1

A. Synthesis of layers of coloured dextran on polymethylmethacrylate 200 mg of dextran (molecular weight about 2,000,000), to which a blue dyestuff (Cibachron blue F36A, CIBA-GEIGY) had been coupled (Blue Dextran 2000, from Pharmacia Fine Chemicals, Uppsala), were dissolved in 5 ml of water. 1 ml of this solution was added to each of four tubes numbered 1-4 and containing 1 ml of 0.4, 2.4 and 6M respectively of sodium hydroxide solution. Four rectangular disks (8×10 mm) of 1 mm thick polymethyl methacrylate (Plexiglass ®, Andrén & Söner, Solna, Sweden) were placed in a glass tube having a tightly closing plug and containing crystals of cyanbromide. After 3 h the disks, which had been impregnated with cyanbromide, were placed in each of the tubes 1-4. After 2 h the solution was sucked off. For hydrolysis of the remaining cyanbromide the disks were repeatedly washed with 0.5M sodium bicarbonate solution and were stored for 24 h in this solution.

B. Characterization of the formed layer

The disks which had been treated as above were rinsed with water and by means of a holder placed perpendicularly to the ray path in a spectrophotometer (Cary 219, Varian AB). The absorbance at 620 nm was read with air as reference. The results are presented under Abs. 1 in Table 1 below. Each of the disks were then incubated overnight in 100 µl of 0.1M sodium phosphate, pH 6.6, containing 100 µg of dextranase (Koch-Light Laboratories Ltd). After rinsing with water the absorbance at 620 nm was again measured in the same manner as above. The results are presented under Abs. 2 in Table 1.

TABLE 1

| Tube No. | Abs. 1 | Abs. 2 | Abs. 2 − Abs. 1 |
| --- | --- | --- | --- |
| 1 | 1.36 | 1.16 | +0.20 |
| 2 | 1.18 | 1.14 | −0.04 |
| 3 | 0.53 | 0.50 | −0.03 |
| 4 | 0.26 | 0.25 | −0.01 |

The values of Abs. 1 show that increasing concentration of NaOH (OH−) during the formation of the layers results in decreasing amounts of dextran in the formed layer, i.e. thinner layers and/or less dense polymers. It is known that the ability of dextranase to hydrolyse cross-linked dextran is reduced when the degree of cross-linking is increased, and the difference in absorbance before and after the dextranase treatment (Abs. 2-Abs. 1) indicates that the formed layer is less cross-linked in its outermost part and that the delimitation against the surrounding solution becomes less pronounced the higher the hydroxide ion concentration is. This is also confirmed by inspection of the layers with the eye.

EXAMPLE 2

A. Synthesis of dextran layers on polymethyl-methacrylate

Thoroughly cleaned square disks (5×5 mm) of 1 mm thick polymethylmethacrylate (Plexiglass ®) are placed in a glass tube having a tightly closing plug and containing crystals of cyanbromide. After 30 minutes the disks were taken out and placed in a tube containing 250 µl of 2M sodium hydroxide solution and 250 µl of a solution of 400 mg of Dextran T 70 (molecular weight about 70,000, from Pharmacia Fine Chemicals, Uppsala) in 10 ml of water. After 10 minutes the solution was sucked off and the disks were repeatedly washed with 0.5M sodium bicarbonate solution.

B. Coupling of antiserum

Half of the disks were treated according to steps a+b+c below, half of them only according to step c. For comparison round disks, diameter 6 mm, were punched out from filtration paper (Munktell OOH, Kebo-Grave) and treated according to steps b+c.

(a) The disks were stored overnight in 0.5M sodium bicarbonate solution.

(b) The disks were transferred to a beaker (immersed in an ice bath) containing 4 ml of 0.5M potassium phosphate solution, pH 11.5, and 1 ml of a solution of 1 g of cyanobromide in 9 ml of water. After 6 minutes the solution was sucked off and the disks were repeatedly washed in ice-cold water.

(c) The disks were transferred to a tube containing 500 µl of antiserum against rabbit IgG (Miles Laboratories) from sheep, diluted 150 times in 0.5M sodium bicarbonate solution containing 0.1% polyoxyethylene(2-)sorbitanmonolaurate (Tween ®20, Atlas Chemical Industries).

After incubation at +4° C. overnight the solution was sucked off and the disks were washed 3×10 minutes with 0.5M sodium bicarbonate solution containing 0.1% Tween ®20, 4 h with 0.1M ethanolamine solution 0.1M with regard to sodium phosphate, pH 8, and 5×30 minutes with 0.1M sodium phosphate solution, 0.15M with regard to sodium chloride and containing 0.5% of Tween ®20, pH 7.4.

C. Preparation of rabbit IgG-125-3

A reaction tube of glass is placed on an ice bath. To the tube are added 50 µl of rabbit IgG ((Miles Laboraties) 1 mg/ml in 0.2M sodium phosphate, pH 7.0), 100 µl of 1.5 mM chloramine T (Merck, pro analysis) and 0.72 µl of Na 125-I 500 mCi/ml (New England Nuclear). After 2 minutes the reaction is stopped by addition of 20 µl of 0.1M sodium sulphate solution and 50 µl of 0.1M potassium iodide solution. The reaction mixture is desalted on a column containing Sephadex G-25 (Pharmacia Fine Chemicals), which has been equilibrated with 0.05M sodium phosphate solution, 0.05M with regard to sodium thiosulphate and containing 0.05% of Tween ®20 and 2% of human serum albumin (Sigma), pH 7.4. The void fraction is diluted 4 times with 0.1M sodium phosphate solution containing 0.1% of Tween ®20, pH 7.5.

D. Uptake of antigen 1 mg of rabbit IgG (Miles Laboratories) was dissolved in 10 ml of 0.1M sodium phosphate solution containing 0.1% Tween ®20, pH 8.40 µl of a solution prepared according to (c) above and containing 10 µg of rabbit IgG-125-I per ml were added.

Each of the three types of disks (from step B) was incubated for 30 minutes in 100 µl of this solution in tubes placed on a shaker (IKA-Vibrax-VXR inst. 1000, Labassco). The disks were washed with 0.3M sodium chloride solution containing 0.5% of Tween ®20, and the remaining radioactivity was measured. A longer incubation time did not result in a higher uptake.

The activity in % of that totally added was 12.9, 4.8 and 5.4 respectively for Plexiglass ® with dextran layer treated according to a+b+c, only according to c, and for paper treated according to b+c respectively. For disks wherein normal sheep serum is coupled instead of antiserum 3.1, 3.0 and 2.1 respectively was obtained.

The results show that the formed layers can be used for immobilization of immunologically active components. The capacity is comparable to that for cyan bromide-activated paper, and it is thus sufficient for performing immunological tests (without BrCN-activation). If a higher capacity is desired, the layer can be activated further in a separate step (step b above).

EXAMPLE 3

A. Formation of dextran layers on various substrates (a) Five square disks (5×5 mm) of 1 mm thick polymethyl methacrylate (Plexiglass ®) were placed in a glass tube having a tightly closing plug and containing crystals of cyan bromide (Polysciences, Warrington, Pa., USA). After 1 h the disks were placed in five tubes (one in each) containing 250 μl of a solution of 400 mg of Blue Dextran 2000 (Pharmacia Fine Chemicals, Uppsala) in 10 ml of water and 250 μl of 0.4M sodium hydroxide solution. The solution was sucked off after 0.5, 2.5, 15 and 60 minutes respectively. The disks were washed repeatedly with 0.5M sodium bicarbonate solution and were stored for 24 h in the solution.

(b) Performed as under (a) but with disks of polycarbonate (Makrolon ®).

(c) Performed as under (a) but with disks of polyvinylchloride.

(d) Performed as under (a) but with discs of polyvinylchloride which had been pretreated (for the purpose of being able to take up more of cyan bromide) by lying for 1 h above the liquid surface—on a bed of glass beads—in a tube with a tightly closing plug containing a few ml of dioxan (Merck, pro analysi).

B. Characterization of the formed layers

The layer-coated disks were rinsed with water and by means of a holder placed perpendicularly to the test ray path in a spectrophotometer (Cary 219, Varian AB). The absorbance at 620 nm was read with air as reference. It appears from the results, which are presented in Table 2 below, that a longer reaction time results in more layer for all of the substrates.

TABLE 2

| Reaction time Minutes | Absorbance at 620 nm | | | |
|---|---|---|---|---|
| | Plexiglass ® | Polycarbonate | PVC | PVC (dioxan treated) |
| 0.5 | 0.74 | 0.32 | 0.13 | |
| 2 | 1.03 | 0.49 | 0.18 | 0.84 |
| 5 | 1.19 | 0.65 | 0.27 | 1.06 |
| 15 | 1.81 | 0.90 | 0.56 | |
| 30 | | | | 1.89 |
| 60 | 2.7 | 1.19 | 0.72 | |

EXAMPLE 4

A. Synthesis of layers of blue dextran (a) 10 g of agarose gel in bead form, 45–165 μm, Sepharose ®-6B, Pharmacia Fine Chemicals) are washed on glass filter with 2.5M phosphate buffer of pH 11.0 (3.33 moles $K_3PO_4$ + 1.67 moles $K_2HPO_4$ per 2 liter of solution adjusted to pH 11.0). The gel is mixed with 20 ml of 2.5M phosphate buffer, pH 11.0, in a beaker. When at least 20 minutes and at most 2 h have passed the gel is sucked off on a glass filter. Cyan bromide (FLUKA) is dissolved to 10% concentration in distilled water (durable for 24 h). A solution of 2.5% of blue Dextran 2000 (Pharmacia Fine Chemicals) is prepared in 0.1M phosphate buffer, pH 7.0, (39 millimoles $NaH_2PO_4$ + 61 mmoles $Na_2HPO_4$ per liter adjusted to pH 7.0). Immediately before use cyan bromide solution is added to the dextran solution to a concentration of 0.5%. 10 ml of this solution is added to each gram of the sucked-off gel according to the above. The gel is gently shaken by hand for 5 minutes. Washing of the gel is carried out on glass filter with distilled water until no blue colour is observed in the washing liquid.

(b) Same procedure as (a) above but using 2.5M phosphate buffer pH 12.0.

(c) 1 g of agarose gel in bead form ("microbeads", 1–2 μm) were washed with 10 ml of 2.5M phosphate buffer, pH 12.0. The washing was done by twice repeated centrifuging and suction-off of the supernatant with a water suction device. The necessary g force on centrifugation of the microbeads was about 6000 g. For each gram of sucked-off gel were added 10 ml of a freshly prepared solution of 2% blue Dextran 2000 with 1% cyan bromide in 0.1M phosphate buffer pH 7.0. This mixture was gently shaken by hand for 5 minutes. The gel was washed with distilled water and centrifuged. This was repeated until no blue colour could be observed in the supernatant.

(d) 10 g of agarose gel in bead form, 45–165 μm, (Sepharose ®-6B, Pharmacia Fine Chemicals, Uppsala) were added to a 20 ml solution of freshly prepared 10% cyan bromide in distilled water. The liquid was sucked off on a glass filter. This was repeated once, followed by repeated addition of the same volume of cyan bromide solution. After 20 minutes the excess of the reagent liquid was sucked off on a glass filter. A solution (2) was prepared with 2% blue Dextran 2000 in 1M NaOH. For each gram of sucked off gel 10 ml of solution (2) were added. The mixture was gently shaken for 10 minutes. The gel was washed on a glass filter with distilled water until no blue colour could be seen in the washing liquid.

(e) 10 g of bead shaped dextran gel cross-linked with epichlorohydrin (dry bead diameter 40–120 μg, Sephadex ®G 75, Pharmacia Fine Chemicals) were added to a freshly prepared 10% cyan bromide solution in distilled water. The procedure was as under (d) above. A solution (2) was prepared from 2.5% blue Dextran 40 (molecular weight about 40,000) in 1M NaOH. The sucked off gel (1 g) was slowly added to a beaker containing 20 ml of solution (2) while stirring (50 rpm) using a propellor agitator. After stirring for 10 minutes at the same rotation speed the gel was washed on a glass filter with distilled water. The washing was repeated until no blue colour could be seen in the sucked off washing liquid.

B. Characterization of the formed layers

For each of the products synthesized according to (a)–(d) above 0.5 g of sucked-off gel were placed in five test tubes, to each of which was added 1 ml of 0.1M phosphate buffer, pH 5.6. A volume of 20 μl of 1 mg/ml dextranase (E.C. 3.2.1.11) having an activity of about 1000 units/mg (Koch Light Laboratories Ltd) was added to each tube. The enzyme activity was stopped, using 0.2 ml of 0.5M NaOH, after 1 minute in tube 1, after 2 minutes in tube 2 and so on to 5 minutes in tube 5. The absorbance at 619 nm was measured in the supernatant liquid. The initial absorbance change is obtained by determining the coefficient of inclination for the ascent of the absorbance curve.

For the syntheses (a) and (b) the initial absorbance change at 619 nm (ΔA 619/minute) was 0.12 and 0.26 respectively. No activity was observed for the synthesis (c).

In 30 minutes dextranase split off all of the blue colour from the gel beads according to syntheses (a) and (b). On the microbeads according to synthesis (c) all colour was split off in 20 minutes.

The product from synthesis (e) was studied by microscopy. Most of the beads had beautiful blue colour, some of them a somewhat weaker colour. No change of the size of the beads could be observed.

EXAMPLE 5

(a) 27 mg of agarose in 10 ml of water were heated while stirring on a boiling water bath until the agarose had melted. The solution was allowed to cool at room temperature over night, whereafter 2.5 ml of 12.5M sodium hydroxide solution were added, and the mixture was stirred vigorously for 1 h (solution I).

A square disk (5×5 mm) of 1 mm thick polymethylmethacrylate (Plexiglass ®) was immersed for 1 h in a solution of 100 mg of cyan bromide in 900 μl of water (solution II).

The disc was rinsed with water, sucked dry and incubated for 2 h without stirring in 500 μl of solution I. The disc was washed repeatedly with 0.5M sodium bicarbonate solution and was stored for 24 h in this solution.

(b) The synthesis was carried out as in (a) above, but the agarose concentration was varied by diluting solution I 2.5 and 10 times respectively with 2.5M sodium hydroxide solution.

(c) The synthesis was carried out as under (a) above, but the cyan bromide concentration was varied by diluting solution II 2.5 and 10 times respectively with water.

(d) The synthesis was carried out as under (a) above, but with the use of a disk of polystyrene. The incubation time in solution II was 5 h.

(e) The synthesis was carried out as under (d) above, but the agarose concentration was varied by diluting solution I 2.5 and 10 times respectively with 2.5M sodium hydroxide solution.

The disks of Plexiglass and polystyrene respectively with layers of agarose, prepared according to (a)–(e) above, were incubated over night in 0.1M etanolamine solution, 0.1M with regard to sodium phosphate, pH 8. Thereafter they were washed with 0.1M sodium phosphate solution, pH 8, containing 0.1% polyoxyethylene(2)sorbitanmonolaurat (Tween ®20, Atlas Chemical Industries).

One disk was sucked off and incubated for 3 h in 100 μl of an about 1 nM solution of rabbit IgG-125-I prepared according to Example 2C (but with 200 times dilution of the void fraction). The disc was removed from the solution by means of a tweezer, was lightly pressed against an absorbing paper, placed in a test tube, and the radioactivity was measured in a gamma counter. The disk was washed 3×30 minutes in 0.3M sodium chloride solution containing 0.5% Tween ®20. The radioactivity was again measured.

The available layer volume V for the labelled protein was calculated as $$V = \frac{\text{(activity before washing)} - \text{(activity after washing)}}{\text{(activity in 100 μl solution)}} \times 100\ \mu l$$

The corresponding layer thickness a mm was calculated from:

$$(5+2a)(5+2a)(1+2a) = (5 \times 5 \times 1) + V.$$

In Table 3 below the layer thickness X is given in μm.

TABLE 3

| Synthesis according to Example | Disk material | Solution I dilution factor | Solution II dilution factor | Available layer thickness μm |
|---|---|---|---|---|
| (a) | Plexiglass | — | — | 9 |
| (b) | " | 2.5 | — | 4 |
| (b) | " | 10 | — | 4 |
| (c) | " | — | 2.5 | 7 |
| (c) | " | — | 10 | 3 |
| (d) | polystyrene | — | — | 12 |
| (e) | " | — | 2.5 | 9 |

TABLE 3-continued

| Synthesis according to Example | Disk material | Solution I dilution factor | Solution II dilution factor | Available layer thickness μm |
|---|---|---|---|---|
| (e) | " | | 10 | 4 |

EXAMPLE 6

(a) 27 mg agarose in 10 ml of water were heated with stirring on a boiling water bath until the agarose had melted. The solution was allowed to cool at room temperature over night. 2.5 ml of 12.5M sodium hydroxide solution were added, and the mixture was vigorously stirred for 1 h (solution I). A square disk (5×5 mm) of 1 mm thick polymethylmethacrylate (Plexiglass ®) was inserted into a glass tube with a tightly closing plug containing crystals of cyan bromide. After 1 h the disk was taken out and incubated for 2 h without stirring in 500 μl of solution I. The solution was sucked off and the disk was repeatedly washed with 0.5M sodium bicarbonate solution and was stored for 24 h in this solution.

(b) 400 mg of dextran (molecular weight about 70,000, Dextran T 70, Pharmacia Fine Chemicals) were dissolved in 5 ml of water. 5 ml of 2M sodium hydroxide solution were added (solution II). A square disk (5×5 mm) of 1 mm thick Plexiglass ® was inserted into a glass tube having a tightly closing plug and containing crystals of cyan bromide. After 30 minutes the disk was taken out and incubated for 10 minutes in 500 μl of solution II. The disk was repeatedly washed in 0.5M sodium bicarbonate solution and was stored for 24 h in this solution.

The disks having layers of agarose and dextran respectively, prepared according to (a) and (b), were treated over night in a 0.1M ethanolamine solution, 0.1M with regard to sodium phosphate, pH 8. Thereafter they were washed with 0.1M sodium phosphate solution, pH 8, containing 0.1% polyoxyethylene(2)sorbitanmonolaurate (Tween ®20, Atlas Chemical Industries). One disk was sucked off and incubated for 3 h in 100 μl of about 1 nM solution of one of the following substances labelled with the radioactive isotope 125-I (molecular weights see Table 4); digoxine, human $\beta_2\mu$ globuline, rabbit-antihuman IgE. The solutions are included as "tracer" in Phadebas ® Digoxin RIA, Phadebas ® $\beta_2$-micro Test and Phadebas IgE PRIST ® respectively (Pharmacia Diagnostics AB). The disk was removed from the solution by means of a tweezer, was lightly pressed against an absorbing paper, placed in a test tube, and the radioactivity was measured in a gamma counter. The disk was washed 3×30 minutes in 0.3M sodium chloride solution containing 0.5% Tween 20. The radioactivity was again measured. The same procedure was performed for the two remaining radioactively labelled substances.

For each labelled substance the available layer volume V and the corresponding available layer thickness were calculated as in Example 5. The results are presented in Table 5.

TABLE 5

| | | Available layer thickness, μm | |
|---|---|---|---|
| Substance | Molecular weight | Ex. (a) agarose | Ex. (b) dextran |
| Digoxin | 781 | 24 | 26 |
| $\beta_2\mu$ globulin | 11600 | 20 | 15 |

TABLE 5-continued

| Substance | Molecular weight | Available layer thickness, μm | |
|---|---|---|---|
| | | Ex. (a) agarose | Ex. (b) dextran |
| Rabbit-antihuman IgG | 150000 | 19 | 17 |

EXAMPLE 7

(a) Synthesis of layers of dextran followed by coloured dextran 400 mg of dextran (molecular weight about 2,000,000, Dextran T 2000, Pharmacia Fine Chemicals) were dissolved in 10 ml of water. 250 μl of this solution were added to each of 3 tubes numbered 1a–3a and containing 250 μl of 0.4, 2 and 6M respectively of sodium hydroxide solution.

400 mg of dextran (molecular weight about 2,000,000), to which a blue dyestuff had been coupled (Blue Dextran 2000, Pharmacia Fine Chemicals), were dissolved in 10 ml of water. 250 μl of this solution were added to each of 4 tubes numbered 1b–3b, 4 and containing 250 μl of 0.4M sodium hydroxide solution.

4 square disks (5×5 mm) of 1 mm thick polymethylmethacrylate (Plexiglass ®) were placed in a glass tube having a tightly closing plug and containing crystals of cyan bromide. After 1 h one disc was placed in each of the tubes 1a–3a. After 1 minute 2.5 ml of water were added, the solution was sucked off and the disks were transfered to tubes 1b–3b. The fourth disk was placed in tube 4. After 10 minutes the solution was sucked off. The disks were repeatedly washed with 0.5M sodium bicarbonate solution and stored for 24 h in this solution.

(b) Synthesis of layers of agarose followed by coloured dextran 27 mg of agarose in 10 ml of water were heated with stirring on a boiling water bath until the agarose had melted. The solution was allowed to cool at room temperature over night. 2.5 ml of 12.5M sodium hydroxide solution were added, and the mixture was stirred vigorously for 1 h (solution I).

Four square disks (5×5 mm) of 1 mm thick polymethylmethacrylate (Plexiglass ®) were inserted into a glass tube having a tightly closing plug and containing crystals of cyan bromide. After 1 h the disks were removed and incubated for 2 h without stirring in 500 μl of solution I. The solution was sucked off and the disks were repeatedly washed with 0.5M sodium bicarbonate solution and stored for 24 h in this solution. The four disks were placed in 1 ml of 12.5, 2, 1 and 0.5M respectively sodium hydroxide solution. After 1 h the solution was sucked off and each disk was placed in 500 μl of a solution of 200 mg of Blue Dextran 2000 and 500 mg cyan bromide in 10 ml of water. After 10 minutes the solution was sucked off. The disks were repeatedly washed with 0.5M sodium bicarbonate solution.

(c) Characterization of the formed layers

The disks which had been treated in accordance with the above were rinsed with water and by means of a holder placed perpendicularly to the test ray path in a spectrophotometer (Cary 219, Varian AB). The absorbance at 620 nm was read with air as reference. The results of synthesis (a) are presented in Table 6, for synthesis (b) in Table 7.

TABLE 6

| Tube No. | $A_{620}$ |
|---|---|
| 1 | 0.53 |
| 2 | 0.66 |
| 3 | 0.85 |
| 4 | 1.21 |

TABLE 7

| NaOH conc. | $A_{620}$ |
|---|---|
| 12.5 M | 5 |
| 2 M | 3.7 |
| 1 M | 2.0 |
| 0.5 M | 0.95 |

EXAMPLE 8

A. Preparation of agarose layers 27 mg of agarose in 10 ml of water were heated with stirring on a boiling water bath until the agarose had melted. The solution was allowed to cool at room temperature over night. 2.5 ml of 12.5M sodium hydroxide solution were added, and the mixture was vigorously stirred for 1 h (solution I).

Four Ellerman-tubes (58×12 mm) of polystyrene (Cerbo, Trollhättan) were washed in water of 70° C. containing 50 ml/l of phosphate-free detergent (Decon 90 ®, Novakemi AB, Enskede). The tubes were thoroughly rinsed with water and allowed to dry. To each tube were added 200 μl of a solution of 1 g cyan bromide in 9 ml of water. After 1 h the solution was sucked off and 100 μl of solution I were added. After 2 h the solution was decanded, the tubes were repeatedly rinsed with 0.5M sodium bicarbonate solution and stored for 24 h filled with this solution.

B. Coupling of allergen 100 mg of birch pollen (from Betula verrucosa, Allergon AB) and 1 ml of 0.1M sodium phosphate solution pH 7.5 were rotated for 2 h at +4° C. After centrifuging the supernatant was removed by pipette and diluted 50 times with 0.1M sodium phosphate solution containing 0.1% polyoxyethylene(2)sorbitan monolaurate (Tween ®20, Atlas Chemical Industries) pH 7.5 (solution II).

The Ellerman tubes treated according to (a) were poured away and placed on an ice bath. 400 μl of 0.5M potassium phosphate solution, pH 11.5, and 100 μl of a solution of 1 g cyan bromide in 9 ml water were added. After 6 minutes the solution was poured away and the tubes were repeatedly washed with ice cold water, whereafter 200 μl of solution II were added. After 4 h the solution was poured away, the tubes were repeatedly washed with 0.1M ethanolamine solution, 0.1M with regard to sodium phosphate, pH 8, and incubated over night in this solution. The tubes were washed further in 0.1M sodium phosphate solution, 0.15M with regard to sodium chloride and containing 0.5% of Tween 20, pH 7.5.

C. Allergy test

The tubes treated according to (b) were poured away and incubated for 3 h with 50 μl of human serum containing birch pollen specific IgE, diluted to 1:1, 1:5, 1:25 and 1:50 respectively with normal human serum (Phadebas RAST ® Reference reagents, Pharmacia Diagnostics AB). The tubes were washed 3×5 minutes with 0.15M sodium chloride solution containing 0.5% Tween 20 (solution III). The solution was poured away, and to each tube were added 50 μl of a solution containing 80 mg of rabbit-anti-human IgE-125-I per ml (Phadebas RAST ® Isotope reagent, Pharmacia Diagnostics AB). After 18 h the tubes were again washed 3×5 minutes with solution III. The solution was poured away, and the remaining radioactivity in the tubes was measured.

The results are reported in Table 8 as the activity in % of that totally added. These values are similar to those which are obtained in the commercial allergy test Phadebas RAST ®, wherein the solid phase is cyan bromide-activated paper disks.

As a comparison the same test was performed with passively adsorptively coated tubes. The coating was done by adding solution II (without Tween 20) to untreated polystyrene tubes, which after incubation over night were washed with 0.1M sodium phosphate solution, 0.15M with regard to NaCl and containing 0.5% Tween 20, pH 7.5.

The allergy test was carried out as under (c) above. The uptake of activity was less than 0.3% of that totally added for passively adsorptively coated disks at all dilutions (i.e not useful values).

TABLE 8

| Allergic test of agarose layers in polystyrene tubes | |
|---|---|
| Dilution: | Uptake, %: |
| 1:1 | 25.8 |
| 1:5 | 10.1 |
| 1:25 | 3.2 |
| 1:50 | 2.4 |

EXAMPLE 9

A thorougly cleaned rectangular disk (20×75 mm) of 1 mm thick Plexiglass ® was placed in a glass tube having a tightly closed plug and containing crystals of cyan bromide. After 1 h the disk was transferred to a beaker, to which had been added 10 ml of 2M sodium hydroxide solution and 400 mg of Dextran T 70 dissolved in 10 ml of water. After 1 h the solution was sucked off. The disk was repeatedly washed in 0.5M sodium bicarbonate solution and was stored for 24 h in this solution.

The disk which has thus been coated with a dextran layer was tested with regard to utility for electrophoresis, the disk being incubated for 2 h in barbital buffer, ionic strength 0.1, pH 8.6 (LKB-Beckman Instruments AB) and was placed on a water cooled plate. Strips of filtration paper impregnated with buffer were placed along the long sides of the disk and were kept moistured during the test. At the middle of the disk was applied 1 μl of a test solution consisting of 18 mg of human serum albumin (Sigma), 6 mg of human methemoglobin (Sigma) and 2 mg of bromophenol blue (Merck) dissolved in 10 ml of barbital buffer. 25 V direct current was applied across the two short end sides of the disk. After 2.5 h two coloured bands were observed about 15 mm (albumin) and 6 mm (hemoglobin) respectively from the starting point in the direction of the positive pole.

We claim:

1. A method of forming at least one polymeric layer on a solid substrate wherein each applied polymeric layer is formed by the cross-linking of an organic substance which can be cross-linked, which method comprises (a) impregnating the solid substrate with at least one component which can control the cross-linking reaction,
(b) contacting the impregnated solid substrate with a surrounding solution so as to form a concentration gradient of at least one of the components which control said cross-linking reaction, and
(c) establishing the concentration gradient so that cross-linking will be restricted to the boundary layer between said solid substrate and said surrounding solution and will not occur throughout the surrounding solution.

2. A method according to claim 1 wherein said at least one polymeric layer is an anistropic polymeric layer.

3. A method according to claim 1 wherein the concentration gradient is achieved by impregnating the substrate with at least one of the components which control the cross-linking reaction and which component on contact of said impregnated substrate with said surrounding solution tends to diffuse into the surrounding solution.

4. A method according to claim 1 wherein said solid substrate is impregnated with a cross-linking agent.

5. A method according to claim 1 wherein a cross-linking agent is present in said surrounding solution, and the solid substrate is impregnated with at least one substance, the concentration of which on the diffusion to the surrounding solution makes possible cross-linking at said boundary layer, whereas its concentration in the surrounding solution prevents cross-linking therein.

6. A method according to claim 1 wherein a pH dependent cross-linking system is chosen, and the pH of the surrounding solution is kept at a value which prevents cross-linking, whereas the pH in the boundary layer makes cross-linking possible.

7. A method according to claim 1 wherein surrounding solution is aqueous and contains a buffer dissolved therein so that substantially no pH gradient can be created in the boundary layer closest to the substrate.

8. A method according to claim 1 wherein the solid substrate is selected from the group consisting of polymethylmethacrylate, polystyrene, polyvinylalcohol, polyvinylchloride, polyethylene, cross-linked dextran and cross-linked poly(hydroxyalkyl methacrylate).

9. A method according to claim 1 wherein the organic substance which can be cross-linked has at least three nucleophilic functional groups, which are amino and/or hydroxyl groups and can react with the cross-linking agent, which is an electrophilic bifunctional cross-linking reagent, under the formation of a three-dimensional hydrophilic network, which can be swollen to a gel.

10. A method according to claim 1 wherein the organic substance which can be cross-linked is a polysaccharide or substituted polysaccharide or a water-soluble derivative of a water-insoluble polysaccharide, a sugar alcohol or a mono, di or oligo saccharide, or a protein.

11. A method according to claim 1 wherein a cross-linking agent is chosen which binds together molecules of the organic substance which can be cross-linked substantially via amide, ether, amine or hydrolytically stable ester bonds or the corresponding stable thioamide, thioether or thioester bonds.

12. A method according to claim 1 wherein the prevention of cross-linking outside said boundary layer is achieved by destruction of the cross-linking ability of said organic substance and/or of the cross-linking agent.

* * * * *